United States Patent [19]

Golias et al.

[11] Patent Number: 4,502,786

[45] Date of Patent: Mar. 5, 1985

[54] METHOD AND APPARATUS FOR AUTOMATED DETERMINATION OF HEMOGLOBIN SPECIES

[75] Inventors: Tipton L. Golias, Beaumont; William T. Mostyn, Jr., Waco, both of Tex.

[73] Assignee: Helena Laboratories Corporation, Beaumont, Tex.

[21] Appl. No.: 106,438

[22] Filed: Dec. 26, 1979

[51] Int. Cl.³ ............................................. G01N 21/00
[52] U.S. Cl. .................................................. 356/435
[58] Field of Search ................ 356/40, 434, 435, 425, 356/436, 411; 250/564, 565, 575, 345

[56] References Cited

U.S. PATENT DOCUMENTS

| | | | |
|---|---|---|---|
| 3,504,978 | 4/1970 | Shibata et al. | 250/564 |
| 3,528,749 | 9/1970 | Bowker | 356/435 |
| 3,678,505 | 7/1972 | Mostyn | 324/99 D |
| 3,684,378 | 8/1972 | Lord | 356/434 |
| 3,810,696 | 5/1974 | Hutchins | 356/435 |
| 3,970,393 | 7/1976 | Krygeris et al. | 356/435 |
| 4,063,817 | 12/1977 | Shimamura et al. | 356/434 |

*Primary Examiner*—Rosenberger R. A.
*Attorney, Agent, or Firm*—Cullen, Sloman, Cantor, Grauer, Scott & Rutherford

[57] ABSTRACT

A method and apparatus for automatically determining the amount of a hemoglobin species in a blood sample in relation to the total amount of hemoglobin in a blood sample by simultaneously determining the relative concentrations of the two samples with a spectrophotometer. The spectrophotometer has two channels each of which is associated with one sample. Each channel determines the intensity of light from a light source which is transmitted through its sample and received by a photodetector. Thereafter, the apparatus calculates the relative concentration of the two samples ($A_1/A_2$) or optionally the normalized concentration of the samples ($A_1/A_1+A_2$). The apparatus includes automatic self-calibration to compensate for any degradation of the optical system.

17 Claims, 5 Drawing Figures

METHOD AND APPARATUS FOR AUTOMATED DETERMINATION OF HEMOGLOBIN SPECIES

CROSS-REFERENCE TO RELATED APPLICATION

The present invention includes the use of automatic self-calibration as described in the copending commonly owned application entitled Automatic Blanking Circuit Ser. No. 106,437, now U.S. Pat. No. 4,257,709.

BACKGROUND OF THE INVENTION

The present invention relates generally to an apparatus such as a spectrophotometer for automatically and simultaneously determining the relative concentration of two samples or solutions. More particularly the present invention may be used for automatically determining the amount of a hemoglobin species in a blood sample relative to the total hemoglobin of the blood sample. The present invention, of course, has a broader applicability than merely hemoglobin ratios. In essence, when measuring the concentrations of two or more solutions for the purpose of an ultimate comparison, it is important that the spectrophotometer not drift or deviate or vary between readings. The present invention overcomes this problem by providing simultaneous measuring of the concentration.

To aid in a complete understanding of the benefit of the present invention, a theoretical explanation of the blood chemistry evaluation will be given. It is known, for example, to prepare blood samples for hemoglobin analyses by a procedure called column chromatography. Column chromatography is used in clinical laboratories to determine levels of various species of hemoglobin in the blood. One such hemoglobin species is Hemoglobin $A_{1c}$ (Hb$A_{1c}$). It has been shown by various investigators that the level of Hb$A_{1c}$ circulating in the blood is an indicator of the status of glucose metabolism in individuals. Determining the percent of the Hb$A_{1c}$ component relative to total hemoglobin aids in the diagnosis and treatment of diabetes (see, for example, R. J. Koenig, C. M. Peterson, et al, *New England Journal of Medicine*, Vol. 295, pp 417–419, Aug. 19, 1976). Methods have been developed for the column chromatographic separation of Hb$A_{1a}$, Hb$A_{1b}$ and Hb$A_{1c}$ as a group from the rest of the hemoglobins using cation exchange chromatography, and the major component of this Hb$A_1$ group is Hb$A_{1c}$. In this technique, the cation exchange may include use of either a cellulosic or non-cellulosic or non-cellulosic cation resin. For example, cellulosic resins were used by Huisman, et al, *Clin. Chim. Act.*, Vol. 5, pp. 103–123, 1960. Additionally, use of cellulose cation exchange resins for the determination of Hb$A_1$ is the subject of U.S. Pat. Nos. 4,142,855, 4,142,856 and 4,142,857. Non-cellulosic cation exchange columns are described by Trivelli, et al, *New England Journal of Medicine*, Vol. 84, pp. 353–357, February 1971, and by M. D. Clegg and W. A. Schroeder, *Journal of the American Chemical Society*, Vol. 83, pp. 1472–1478, 1961, and are the subject of U.S. Pat. No. 4,142,858. These procedures all require separation of two blood fractions using an ion-exchange column, followed by separate measurements and calculations to arrive at a numerical value of Hb$A_1$.

Still another hemoglobin species is Hemoglobin $A_2$ (Hb$A_2$). Determining the amount of Hb$A_2$ present in blood provides an aid to the physician in diagnosing disorders of the red blood cells, especially the genetic disorder B-Thalassemia. Hb$A_2$, like Hb$A_1$, may be determined by column chromatographic techniques using ion-exchange chromatography (see for example, E. C. Abraham, *Hemoglobin*, Vol. 1, pp. 27–44 1976). As in the Hb$A_{1c}$ procedure, the Hb$A_2$ procedure requires many manipulations and measurements following the step of chromatographic separation.

In order to understand the nature of the calculations and manipulations which must be made after the column chromatographic separation, it should be understood that when measuring the concentration of a substance, such as hemoglobin in solution, the concentration of the substance measured photometrically usually follows Beer's Law where the negative logarithm of the transmittance of light through the sample varies as a function of the concentration. Specifically, the formula is $\log(I/I_o) = -kC$ where the ratio $(I/I_o)$ is referred to as the transmittance or percent of light which is not absorbed by the sample. Thus, in the formula, the transmittance $I/I_o$ is the ratio of the intensity of a beam of light passing through the solution divided by the intensity of the same beam of light passing through a solution containing a zero concentration of the substance to be measured. A solution containing a zero concentration of the substance to be measured is referred to as a "blank" solution.

Thus it may be appreciated that when the relative concentration of hemoglobins as between two samples is to be measured and calculated, the value of the transmittance, $I/I_o$, must be determined for each sample.

For example, to determine the amount of hemoglobin Hb$A_2$ as a percent of the total hemoglobins in the blood, two samples must be prepared such as by column chromatography, the first sample containing only Hb$A_2$ and the second sample containing the remaining hemoglobins. Each sample is then separately placed in a spectrophotometer. For the first sample, the values $I$ and $I_o$ are determined. Then the values $I$ and $I_o$ are determined for the second sample. Then the percent of hemoglobin Hb$A_2$ is calculated according to the formula $$\frac{\log(I/I_o)HbA_2}{\log(I/I_o)HbA_2 + \log(I/I_o) \text{ remaining hemoglobins}}$$

According to the prior art, each of the measurements required by the above formula were separately determined and this created inherent variations because of changes in the optical system such as those occasioned by drift of the spectrophotometer as well as degradation of the optical system. We have discovered that the problems of the prior art technique may be eliminated by the present invention which provides two channels to simultaneously measure the transmittance of the two samples using a single light source.

Another problem with prior art techniques was that even when the transmittance of a single sample was being determined there could be degradation of the optical system between the time of calibration of the system and the time at which the transmittance of light through a particular sample was being measured. The co-pending application referred to above addresses itself to an automatic blanking circuit for effectively self-calibrating the spectrophotometer automatically and the features of automatic blanking are preferably included in the method and apparatus of the present invention.

Thus the present invention provides an improved method and apparatus for determining the relative concentration of two samples by providing for the simultaneous measurement of the concentration of each sample using a single source of light.

SUMMARY OF THE INVENTION

The present invention provides a method and apparatus for simultaneously determining the relative concentrations of two solutions or samples which may be used with a spectrophotometer or other optical detection system using a single source of light and means for splitting light from the source into two paths, each path having a photodetector associated therewith to measure the intensity of light transmitted through the solution or sample. The present invention includes two channels, each of which is associated with one of the photodetectors, and each channel includes means to receive the output from the photodetector, means to compare the output from the photodetector to a reference value and, analog to digital conversion means to provide a value indicative of the intensity of light transmitted through the sample.

In addition, the present method and apparatus includes the automatic blanking of the aforementioned co-pending application so that during those intervals when the intensity of light through the sample is not being measured because of the absence of a sample, self calibration occurs to provide an up-dated value of $I_o$ so that in all instances any degradation of the optical system is automatically accounted for.

According to the present invention, the automatic blanking occurs whenever there is no vial in the spectrophotometer and the intensity of the light source reaching the photodetector ($I_o$) is determined approximately twice per second. The eleven most recent determinations of light intensity are stored and when a vial containing a sample is to be inserted into the instrument, the system automatically calculates the average intensity of the seven oldest readings in storage to accurately determine the most recent reliable value of $I_o$. In actual use in a spectrophotometer the value log $(I/I_o)$ is actually determined as log $I -$ log $I_o$. Hence the automatic blanking feature repeatedly determines the value log $I_o$ when there is no vial in the instrument and the value of log $I_o$ is stored. According to the present invention, this automatic blanking occurs simultaneously for each of the two channels.

According to the present invention, when the two samples in their respective vials are placed in the spectrophotometer, the intensity of light reaching each photodetector (referred to as $I_a$ and $I_b$ respectively) is determined approximately twice per second. The method and apparatus of the present invention automatically calculates the values of $I_a$ and $I_b$. Then, depending on which of two options are selected, the method and apparatus of the present invention provides an output indicating the relative concentration of each of the two samples:

$$\frac{\log(I_a/I_o)}{\log(I_b/I_o)},$$

or the normalized concentration:

$$\frac{\log(I_a/I_o)}{\log(I_a/I_o) + \log(I_b/I_o)}$$

BRIEF DESCRIPTION OF THE DRAWINGS

The various objects, benefits and advantages of the present invention, together with other objects and advantages which may be attained by its use, will become more apparent upon reading the following detailed description taken in conjunction with the drawings.

In the drawings, where like reference numerals identify corresponding components.

DETAILED DESCRIPTION OF THE INVENTION

Figure 1:
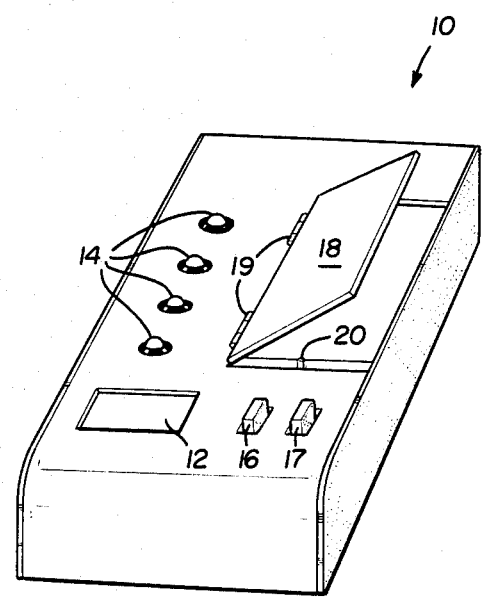
FIG. 1 is a perspective illustration of a spectrophotometer according to the principles of the present invention.

With reference to the drawings FIG. 1 illustrates generally a spectrophotometer 10 which includes the apparatus of the present invention and which can thus be used to practice the method of the present invention. The spectrophotometer has provisions to receive a plurality of vials and to provide a visible digital display 12 indicative of the relative or normalized concentration of the solutions being evaluated. The spectrophotometer has a plurality of indicator lights 14 which are used to reflect the status of the equipment and a pair of push button switches 16, 17, the purpose of which are explained herein.

In a preferred embodiment, the four indicator lights 14 may provide a first light to indicate that the machine is warming up, a second light where relative concentration between two samples is being calculated, a third light where the normalized concentration of a sample is being determined and a fourth light to indicate an error condition. The error condition could occur if there is a failure in the light source, photodetector or electronics of the present invention or a misalignment of the optical system, etc. The switch 16 may be used as a check switch to be depressed for testing out the system and the second switch 17 is used to switch between the two modes of computation, relative concentration or normalized concentration. The spectrophotometer further includes a lid 18 hinged at 19 to open and close and in connection with the lid a normally open limit switch 20 is provided. The switch 20 is normally opened when the lid 18 is closed and hence switch 20 is closed by lifting or opening the lid 18 of the spectrophotometer.

Figure 2:
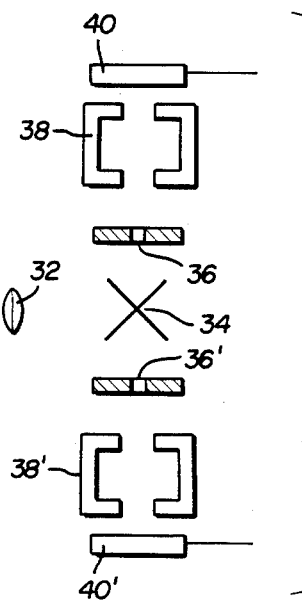
FIG. 2 is a diagramatic view of the optical system of the present invention illustrating the use of a single source of light split into two paths for simultaneously transmitting light through each of two samples.

Turning next to the optical system of the present invention, this is illustrated diagramatically in FIG. 2 where a single light source 30 provides light rays which are focused by a lens and filter system 32 and directed at a beam splitter means 34. From the beam splitter means 34 two beams of light emanate in opposite directions. One of the beams of light from the beam splitter means 34 extends through a first diaphragm or slit 36 and through a well 38 or receptacle positioned to receive a vial of the solution or sample to be tested. The well 38 supports the vial so that the light which passes through the slit 36 may also pass through the vial. Positioned on the opposite side of the well 38 from the slit 36 is a photodetector 40 which provides an output signal indicative of the amount of light received through the vial. As is well known, the photodetector provides an output current having an intensity proportional to the intensity of light received by the photodetector.

The spectrophotometer of the present invention also includes means to simultaneously determine the concentration of a second sample. Hence there is also provided, as illustrated in FIG. 2, a second diaphragm or slit 36' positioned between the beam splitter means 34 and a second well 38' which also receives a vial. A second photodetector 40' is positioned on the opposite side of the well 38' from the beam splitter 34 such that the second photodetector 40' receives the light transmitted through the second sample or solution.

Figure 3:
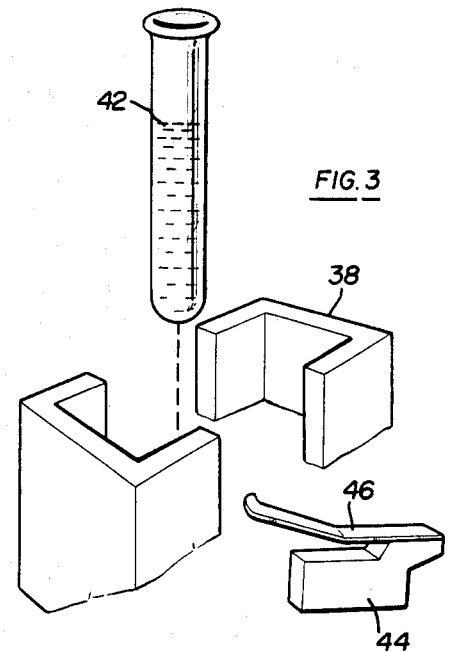
FIG. 3 is a perspective illustration, partly broken away, of the physical location of a sensing switch relative to the holder for the samples.
Figure 4:
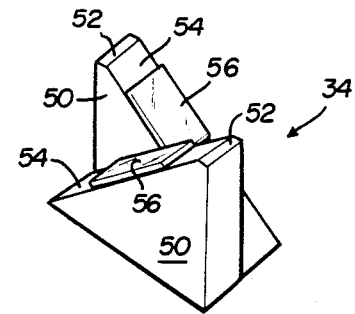
FIG. 4 is a perspective illustration of the mirror system for splitting the light from the light source into two paths.

FIG. 3 illustrates, generally, one of the wells 38 for receiving a vial 42. Positioned beneath the well 38 is a normally closed sensing switch 44. Switch 44 is a conventional limit switch or microswitch which includes an elongated arm 46 which extends beneath the well so that upon insertion of the vial 42 into the well 38, the vial pushes on the arm 46 to open the normally closed switch 44. The second well 38' has associated therewith a switch 44' with an elongated arm 46'.

One of the novel features of the present invention is the beam splitter means 34 which reflects the parallel rays of light received from the light source 40 into two opposite directions so that the same source of light may be utilized to simultaneously determine the concentration of each of two solutions. In a preferred embodiment, the beam splitter means 34 comprises a pair of thick plates 50 each of which is formed as an isosceles right triangle having an upper corner truncated as at 52. Positioned on the inclined surface 54 of each triangle, which inclined surface corresponds to the hypotenuse of the right triangle, is a thin front surfaced mirror 56. Each of the right triangular plates 50 are identical and one triangular plate is reversed relative to the other in assembly so that the planes of the surfaces of the mirrors are at right angles relative to each other. Hence the light which is aimed at an angle of 45° relative to the surface of each mirror is thus split into two paths 180° apart.

In order to understand the circuit of the present invention, it must be appreciated that when vials are placed in each of the two wells 38, 38', there is a simultaneous evaluation of the intensity of light transmitted through each vial. To reduce the opportunity for error in the use of the equipment it is preferable to utilize a small diameter vial and a large diameter vial where the small diameter vial contains the hemoglobin which is removed by the column chromatography technique and the large vial contains the remaining hemoglobins. For the purpose of explanation, it will be assumed that the smaller vial is placed in well 38 and the larger vial in well 38'. Each vial, when inserted in its respective well, will contact its respective limit switch 44, 44' and open such limit switch.

Figure 5:
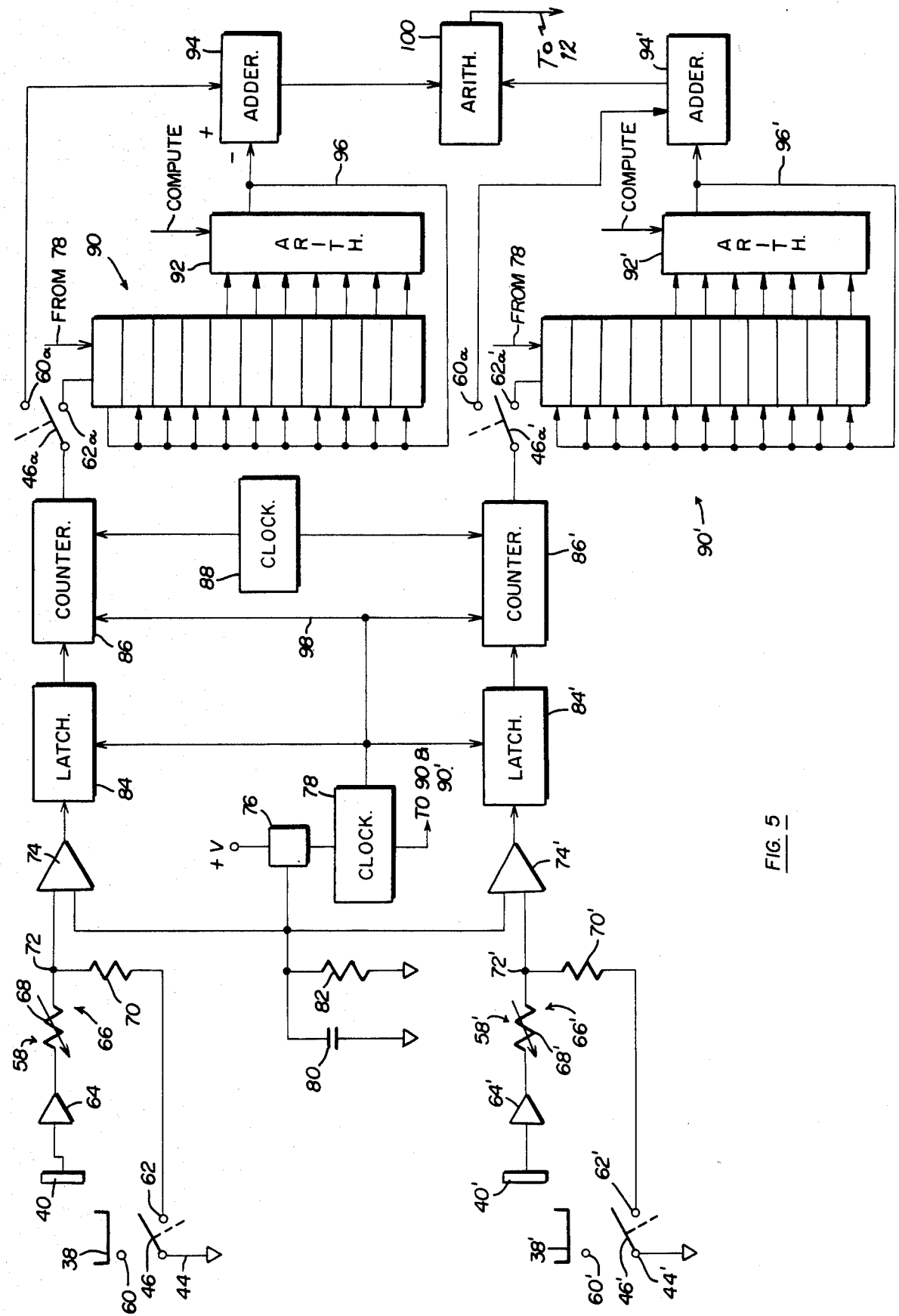
FIG. 5 is a circuit diagram for the method and apparatus of the present invention.

With reference to FIG. 5, the circuit of the present invention will now be explained. Since the spectrophotometer of the present invention provides for the measurement of concentration of two concentrations simultaneously, there are two identical electrical channels each associated with one of the photodetectors 40, 40', and only one such channel will be described in connection with the well 38 and the photodector 40. In addition, those circuit components which are common to both channels will also be explained. It should be appreciated, however, that the electrical components and channel associated with photodetector 40 are identical to the components associated with photodetector 40'. Hence the components of the channel associated with the photodetector 40' are illustrated in the drawing with the superscript 1.

Prior to an explanation of FIG. 5, it should be recalled that the logarithm of the transmittance $(I/I_o)$ varies negatively with the concentration. Thus the present system, while determining the intensity of light reaching the photodetector, uses a logarithmic conversion with respect to a reference voltage to provide the desired output system. Such a logarithmic conversion is explained in greater detail in U.S. Pat. No. 3,678,505. With respect to the channel associated with photodetector 40, the output of the photodetector, which is a signal varying in intensity with the light received, is coupled to an amplifier means 58. As indicated previously a switch 44 is positioned in the bottom of the well 38, the switch having two terminals 60 and 62. The switch 44 is a normally closed switch with the wiper connected to terminal 62 when the switch is closed. The switch is opened when the vial is inserted in the well and this causes the wiper arm of the switch to move from the terminal 62 to terminal 60.

The amplifier means 58 includes an amplifier 64 which receives its input from the output of the photodetector 40. The output of the amplifier 64 is coupled through a voltage divider 66 comprising the combination of a first resistor 68 such as a potentiometer and a second resistor 70. One side of resistor 70 is connected to resistor 68 and the other side of resistor 70 is connected to the terminal 62 of the switch 44. The output from the amplifier means 58 is taken from the junction 72 of the two resistors which comprise the voltage divider. This output from junction 72 serves as one input to a dual or two-input comparator 74. The other input to the two-input comparator 74 is a logarithmically decaying voltage which is provided by a reference voltage means. Specifically, when a switch 76 is closed and opened by pulses from a first clock 78, a voltage is supplied through the switch 76 to one side of a capacitor 80. The other side of capacitor 80 is coupled directly to system ground. A resistor 82 is connected in parallel between the switch 76 and ground across the capacitor 80 to provide a discharge path for the voltage on the capacitor 80. The second input to the comparator 74 is taken from the junction of capacitor 80 and resistor 82.

An analog to digital conversion means is provided to convert the output of the comparator 74 into a digital value representative of the time during which the light received by the photodetector 40 is less than the voltage on the discharging capacitor 80. Specifically, the output from the comparator 74 is coupled to close a latch 84. The output of the latch 84 is connected as the starting signal to a digital counter 86. A second clock 88 providing pulses at a clock rate of 7500 per 512 milliseconds provides the pulses to be counted by the counter 86. The first clock 78, which provides one pulse having a duration of 20 milliseconds every 512 milliseconds, controls the recharging of the capacitor 80 as previously described, and also opens the latch 84 on the trailing edge of that 20 millisecond pulse. Thus, the latch is opened by the pulse which recharges the capacitor and closed by the output of the comparator 74. Since the first clock 78 provides a pulse every 512 milliseconds (approximately twice per second) the value of transmitted light is thus being repeatedly counted approximately twice per second.

With the lid or cover 18 closed and no vials in the wells, the systems blanks or self calibrates once every 512 milliseconds as described in the copending application and each of the successive values counted by the counter 86 is serially stored in a storage means. Specifically, the output from the counter 86 is in response to a pulse from clock 78 into a memory 90 which memory serially stores eleven sequential outputs from the counter 86. Memory 90 functions as a serial shift register so that as a new output is received from the counter 86 every 512 milliseconds, the pre-existing outputs stored in memory 90 are each shifted serially down one level. Since value in the lower most level of the shift register memory 90 cannot be shifted, then when a new value is shifted into the lower most level of the memory 90 the pre-existing value in such lower most level is discarded.

According to the principles of the present invention, means are also provided to obtain an average value of the intensity of the light received by the photodetector. In a typical clinical laboratory instrument such as a spectrophotometer, the instrument lid or cover 18 is to be closed both when the concentration of the sample in the vial 42 is being measured and when the instrument is being blanked or self-calibrated. Opening the cover permits extraneous light, other than light from the source 30, to be received by the photodetector 40. Accordingly, a more reliable determination of the intensity of the light received by the photodetector during self-calibration may be obtained by ignoring the most recent readings from the counter 86 which are stored in memory as these are most likely to be at least partially the result of extraneous light as the cover or lid of the instrument is being opened.

Thus, in accordance with the aforementioned principles of ignoring the most recent readings from the counter 86, the invention includes arithmetically averaging certain of the values in the memory 90 for self-calibration. In the preferred embodiment, where eleven different values are stored in the memory, the seven oldest values are averaged. This is done in an arithmetic unit 92 which could be a combination of a summing circuit and a dividing circuit. The result of the arithmetic operation is provided as the negative input to an adder means 94 and as an input back to all eleven levels of the serial shift register memory 90 via lead 96.

Prior to explaining the operation of the circuit in greater detail, one additional feature should be explained. This feature, which is optional, involves a preferred factory or initial adjustment which needs to be performed one time only when the circuit is being utilized in a spectrophotometer. Specifically, it should be appreciated that if a vial 42 of clear water is inserted in the well 38 there may be a slight absorption of light from the source 30. It is preferred to account for such slight absorption of light by providing an adjustment in the voltage divider 66 such that the output of the amplifier means 58 at the junction 72 is the same when no vial is in the well 38 as when a vial of water (also known as zero concentration) is in the well. To accomplish this initial adjustment, a voltmeter may be connected at the junction 72 and a vial 42 of clear water inserted in the well 38. The insertion of the vial in the well moves the wiper arm of switch 44 to terminal 60 so that resistor 70 is not part of the voltage divider circuit. The voltage at junction 72 is determined and then the vial is removed from the well thereby causing the switch 44 to revert to its normally closed position at terminal 62 thus making resistor 70 a part of the circuit. The potentiometer 68 is now adjusted to provide the same reading on the voltmeter at junction 72. In this way, the voltage at junction 72 is always the same whether there is a vial of zero concentration in the well or whether there is no vial in the well.

With the foregoing as a description of one channel of the electrical circuit, and recognizing that the channel associated with well 38' and photodetector 40' is the same, the operation of the circuit will now be explained. Recalling that for each individual channel the transmittance is to be determined as log $(I/I_o)$ which is log $I - \log I_o$, the first step is to compute the value of $I_o$ for each channel. To compute this value of $I_o$, indicating a zero solution or no vial in the wells 38 and 38', the lid 18 is closed thereby opening the normally opened microswitch 20. The first clock 78 provides a 20 millisecond pulse and the voltage through switch 76 charges the capacitor 80. Since the first clock 78 has a pulse rate of one 20 millisecond pulse every 512 milliseconds, which is approximately one pulse every one-half second, the operation of each channel of the circuit during the next one-half second will now be explained. The charge or voltage on the capacitor 80 starts to discharge or decay through the resistor 82. During the time that the intensity of light received by the photodetector 40 and amplified by the amplifier means 58 and thereafter provided as one input to the comparator 74 is less than the decaying voltage on the capacitor 80, the latch 84 is open and the counter 86 starts counting pulses at a rate of 7500 pulses per 512 milliseconds. As soon as the charge on the capacitor drops below the voltage supplied to the comparator 74, the output of the comparator 74 goes low thus closing the latch 84 so that the counter 86 is no longer incremented. On the leading edge of the next pulse from the first clock 78, the value in the counter is shifted into memory 90 and the counter is reset by the clock pulse on lead 98. The operation is repeated during the next 512 millisecond interval with a charging of the capacitor 80 and a counting by the counter 86 at the rate of 7500 clock pulses per 512 milliseconds, the time during which the voltage on the capacitor exceeds the amplified voltage at junction 72. At the end of the next 512 millisecond interval, the output of the counter is shifted into the memory 90 and each value already in memory 90 is shifted down one level.

At the time when the lid or cover 18 of the spectrophotometer instrument is lifted, the microswitch 20 is closed thus providing a "compute" signal to the arithmetiic unit 92. This causes the arithmetic unit 92 to average the seven oldest values in the shift register memory 90 to provide an output value to adder means 94 and simultaneously that average value is entered, along lead 96 back into all eleven levels of the shift register.

Thus, as a first step, the present invention determines the value of log $I_o$ for each channel once every 512 milliseconds and stores the eleven most recent values in memory. These eleven values occurred during the preceding 11×0.512 or 5.632 seconds. Then, in response to a compute signal, the seven oldest values are averaged. In so doing, the four most recent values, which occurred during the preceding 4×0.512 or 2.048 seconds are ignored, thus preventing the act of opening the lid 18 from introducing error into the determination of $I_o$.

Thus, this first step automatically adjust for degradation of the optical system by providing, automatically, the equivalent of a calibration.

Having thus completed the explanation of the invention as each channel calibrates the value of log $I_o$, the next step in the use of the spectrophotometer would be to insert the vials 42, 42' into the wells 38, 38' respectively. Inserting the vials into the wells moves the switches 44 and 44' to the terminals 60, 60'. Upon closing the lid 18 thus opening the normally open switch 20, the present invention calibrates the value of log I and does the desired computations as follows:

Clock 78 provides a pulse of a 20 millisecond duration allowing the voltage through switch 76 to charge the capacitor 80. As previously indicated, the clock 78 generates a pulse every 512 milliseconds which is approximately one pulse every one-half second and the operation of the circuit during the next one-half second will be explained. Basically, the operation of the circuit is the same as previously described when there were no vials in the wells. However, since there are vials in the wells at this time, each photodetector 40, 40' will receive a lesser amount of light than when the wells were empty and since switch arm 44 is now at terminal 60, the output signal from the amplifier 64 will not be diminished since resistor 70 is no longer connected to ground. During the next one-half second, the intensity of light received by each photodetector is amplified by the amplifier means 58, 58' and thereafter provided as one input to each comparator 74, 74' respectively. During the time the input to the comparator is less than the decaying voltage on the capacitor 80, the respective latches 84, 84' are open and the counters 86, 86' count pulses at a rate of 7500 pulses per 512 milliseconds. As soon as the charge on the capacitor 80 drops below the voltage supplied to each comparator, the output of that respective comparator goes low thus closing its associated latch so that the associated counter in that particular channel is no longer incremented.

Each switch 44, 44' is illustrated in FIG. 5 as being a double pole, double throw switch. When switch arm 46 is at terminal 62, the corresponding arm 46a is at terminal 62a and the output of the counter 86 is an input to memory 90. Similarly when switch arm 46' is at terminal 62', the corresponding arm 46a' is at terminal 62a'.

On inserting a vial in each well, as switch arms 46 and 46' move to terminals 60 and 60', respectively, the corresponding switch arms, 46a and 46a' move to terminals 60a and 60a' respectively. Thus on the leading edge of the next pulse from the clock 78, the value in each counter is shifted to the positive side of its associated adder 94, 94' and the counter is reset by the clock pulse on lead 98. This operation is repeated with vials in the well during the next 512 millisecond interval with a charging of the capacitor 80 and a counting by each counter 86, 86'.

Since log $(I/I_o)$ may be determined as log I − log $I_o$, the adder means 94 is actually determining log $(I/I_o)$ once every 512 milliseconds, since the value of log $I_o$ from memory 90 is connected to the negative side of adder means 94 and the value of log I is connected to the positive side of adder means 94. The same determination is, of course, being performed simultaneously for the second channel by adder means 94'.

The output from each adder means 94, 94' is connected to an arithmetic unit 100. Depending upon which mode of operation has been selected, the arithmetic unit 100 now provides the necessary computation. If relative concentration is to be determined, the value of log I − log $I_o$ for one channel is divided by the value of log I − log $I_o$ for the other channel and a numerical reading is provided to the display 12.

If, however, the mode select switch 17 has been actuated so that a normalized concentration is desired, then the arithmetic unit 100 will take the transmittance of the sample in one channel and divide that value by the summation of the transmittance of the samples of both channels. Thus once every 512 milliseconds the output from the arithmetic unit 100 is displayed by the display means 12. Hence the display is on a real-time basis and may actually change once every 512 milliseconds as long as the lid 18 is closed and the vials are in the wells.

Thereafter, when lid 18 is opened and the vials removed, switch arms 46 and 46a move back to terminals 62 and 62a, and switch arms 46' and 46a' move back to terminals 62' and 62a' and the self-calibration is performed automatically upon closing lid 18 with the wells 38, 38' empty.

In the preferred embodiment of the present invention, all of the clocking and pulsing functions as well as counting, storage, adding, memory shifting and arithmetic computations will be performed on a microprocessor such as a Motorola 6800 or Motorola 6802. However, for the purposes of completeness the above circuit description which includes the use of off-the-shelf components, has been given.

The foregoing is a complete description of a preferred embodiment of the present invention. Various changes and modifications may be made without departing from the spirit and scope of the present invention. For example, multiple channels, in excess of two may be provided so that multiple samples may be simultaneously evaluated. Accordingly, the present invention should be limited only by the scope of the following claims.

What is claimed is:

1. Apparatus for simultaneously determining the relative concentration of two solutions each of unknown concentration comprising:

a single source of light;

a source of reference voltage;

first conversion means responsive to the source of reference voltage and to the amount of light from said light source transmitted through one of said two solutions of unknown concentration for repeatedly determining the concentration of said one solution;

second conversion means responsive to said source of reference voltage and to the amount of light from said light source transmitted through the other of said two solutions of unknown concentration for repeatedly determining the concentration of said other solution; and arithmetic means simultaneously receiving inputs from each of said first and second conversion means for repeatedly determining the relative concentration of said two solutions.

2. Apparatus for simultaneously determining the relative concentration of two solutions each of unknown concentration comprising:

an optical system including a light source, means for splitting light from said light source into two paths, and first and second photodetectors each of said photodetectors providing an output proportional to the amount of light from said light source which is transmitted through one of said two solutions of unknown concentration;

a source of reference voltage;

dual channel conversion means each channel simultaneously receiving an input from said source of reference voltage and the output from a different one of said photodetectors;

each of said dual channel conversion means for repeatedly simultaneously providing an output; and first arithmetic means repeatedly receiving an input from the output of each channel of said dual channel conversion means for repeatedly determining the relative concentration of said two solutions.

3. The invention as defined in claim 2 wherein each channel of said dual channel conversion means includes dual input comparator means receiving a first input from said photodetector and a second input from said source of reference voltage, said dual input comparator means providing an output when the reference voltage exceeds the photodetector output; and counter means for measuring the time interval during which said comparator means provides an output;

the output of the counter means of each of said dual channel conversion means being connected to said first arithmetic means.

4. The invention as defined in claim 1 wherein said storage means of each channel also receives the output from said arithmetic averaging means associated therewith.

5. The invention as defined in claim 2 wherein said source of reference voltage is a single source of reference voltage for supplying an input to the comparator means of each channel of said dual channel conversion means.

6. The invention as defined in claim 2 wherein said source of reference voltage provides an exponentially decaying voltage.

7. The invention as defined in claim 2 wherein said light splitting means includes a pair of mirrors positioned at an angle relative to each other for splitting said light from said light source into opposed paths.

8. The invention as defined in claim 2 wherein a portion of said apparatus also functions in the absence of any solutions to provide an indication of the light received by the first and second photodetectors said portion including first and second storage means each for serially receiving and storing a first selected plurality of sequential outputs from one channel, respectively, of said dual channel conversion means; and second and third arithmetic means each for averaging selected values from one of said first and second storage means.

9. The invention as defined in claim 2 wherein each channel of said dual channel conversion means includes adder means, said adder means receiving a plurality of signals indicative of the concentration of the solution associated with such channel and a signal indicative of the light received by the photodetector associated with said channel in the absence of a solution;

the output of each adder means being coupled to said first arithmetic means.

10. Apparatus for simultaneously determining the relative concentration of two solutions each of unknown concentration comprising:

an optical system including a single light source, means for splitting light from said light source in two paths, and first and second photodetectors each of said photodetectors providing an output proportional to the amount of light from said light source which is transmitted through one of said two solutions of unknown concentration;

a source of reference voltage;

dual channel electrical conversion means, each channel simultaneously repeatedly receiving an output from a different one of said photodetectors, each of said channels including comparator means to compare the reference voltage to the output of the respective photodetector; an analog to digital converter for providing a digital value representative of the time during which the reference voltage exceeds the intensity of light received by said photodetector; first storage means for serially storing a first predetermined number of selected outputs from said analog to digital converter in the absence of a solution; and means for averaging a second predetermined number of values in said first storage means and providing an output, said second predetermined number being less than said first predetermined number, adder means for receiving second signals from said analog to digital converter in the presence of solutions and for receiving the output from said averaging means; and first arithmetic means for comparing the outputs from each of said channels for repeatedly determining the relative concentration of said two solutions.

11. The invention as defined in claim 10 wherein the reference voltage is provided by a single source coupled to each of said comparator means.

12. The invention as defined in claim 10 wherein said source of reference voltage is a single source providing an exponentially decaying voltage.

13. The invention as defined in claim 10 wherein said light splitting means includes a pair of mirrors positioned at right angles to each other.

14. A method for simultaneously determining the relative concentration of two solutions each of unknown concentration comprising the steps of:

providing an optical system including a light source and first and second photodetectors;

splitting the light from said light source into two paths;

providing a source of reference voltage;

comparing the reference voltage to the output of said first photodetector;

simultaneously comparing the reference voltage to the output of said second photodetector;

separately simultaneously and repeatedly deriving digital values representative of the time during which the reference voltage exceeds the intensity of light received by each photodetector said digital values being proportional to the actual concentration of each of said two solutions of unknown concentration; and comparing said derived digital values from one of said photodetectors with said derived digital values from the other of said photodetectors for providing an output indicative of the relative concentration of said two solutions.

15. The invention as defined in claim 14 wherein each step of separately deriving digital values includes the steps of:

serially storing a first selected predetermined number of said digital values with respect to the first photodetector in the absence of a first solution;

averaging a second predetermined number of the serially stored values and providing an output;

serially storing a first selected predetermined number of said digital values with respect to said second photodetector in the absence of a second solution; and averaging a second predetermined number of the serially stored values associated with said second photodetector and providing a second output;

each of said steps of serially storing being simultaneously performed; and each of said steps of averaging being performed simultaneously.

16. The invention as defined in claim 15 wherein, for each solution, said averaged values are subtracted from said digital values prior to comparing said separately derived digital values.

17. The invention as defined in claim 14 wherein a single source of reference voltage is provided.

* * * * *